(12) United States Patent
Mu (10) Patent No.: US 11,684,329 B2
(45) Date of Patent: Jun. 27, 2023

(54) COLLIMATOR AND DETECTOR BASED MEDICAL IMAGING SYSTEMS

(71) Applicant: Argospect Technologies Inc., Foster City, CA (US)

(72) Inventor: Zhiping Mu, Foster City, CA (US)

(73) Assignee: ARGOSPECT TECHNOLOGIES INC., Foster City, CA (US)

( * ) Notice: Subject to any disclaimer, the term of this patent is extended or adjusted under 35 U.S.C. 154(b) by 0 days.

(21) Appl. No.: 17/563,640

(22) Filed: Dec. 28, 2021

(65) Prior Publication Data

US 2022/0117567 A1    Apr. 21, 2022

Related U.S. Application Data (62) Division of application No. 16/676,932, filed on Nov. 7, 2019, now Pat. No. 11,213,262.

(60) Provisional application No. 62/760,659, filed on Nov. 13, 2018, provisional application No. 62/758,183, filed on Nov. 9, 2018.

(51) Int. Cl.
*A61B 6/00* (2006.01)

(52) U.S. Cl.
CPC .......... *A61B 6/4291* (2013.01); *A61B 6/4266* (2013.01); *A61B 6/502* (2013.01); *A61B 6/461* (2013.01)

(58) Field of Classification Search
CPC ....... G01T 7/005; G01T 1/2985; G01T 1/161; A61B 6/4291; A61B 6/461; A61B 6/4266; A61B 6/502; A61B 6/06; A61B 6/08; G21K 1/02; G21K 1/025; G21K 1/04; G21K 1/00

See application file for complete search history.

(56) References Cited

U.S. PATENT DOCUMENTS

| | | | |
|---|---|---|---|
| 6,737,652 B2 | 5/2004 | Lanza et al. | |
| 7,989,771 B2 | 8/2011 | Wieczorek et al. | |
| 8,121,249 B2 | 2/2012 | Wang et al. | |
| 8,483,352 B2 | 7/2013 | Hoffman et al. | |
| 9,263,160 B2 | 2/2016 | Kang et al. | |
| 10,371,832 B1 | 8/2019 | Hugg | |
| 2007/0040124 A1 | 2/2007 | Accorsi | |
| 2010/0310037 A1 | 12/2010 | Wang | |
| 2011/0158384 A1 | 6/2011 | Beekman | |

(Continued)

FOREIGN PATENT DOCUMENTS

| | | |
|---|---|---|
| CN | 102551761 A | 7/2012 |
| CN | 103220978 A | 7/2013 |

OTHER PUBLICATIONS

Weinmann, Amanda L. et al., "Design of optimal collimation for dedicated molecular breast imaging systems", Mar. 2009, American Association of Physicists in Medicine, vol. 36, No. 3, pp. 845-856.

(Continued)

*Primary Examiner* — Don K Wong
(74) *Attorney, Agent, or Firm* — Haynes and Boone, LLP (57) ABSTRACT

A breast imaging system for examining a breast on a chest of a patient comprises first one or more shielding devices configured for placement on a first side of the breast and a first collimator and a first detector configured for placement on the first side of the breast and at a position that is further away from the breast and from the chest than the first one or more shielding devices are.

20 Claims, 7 Drawing Sheets

(56) References Cited

U.S. PATENT DOCUMENTS

| | | |
|---|---|---|
| 2011/0268339 A1 | 11/2011 | Volokh et al. |
| 2012/0181457 A1* | 7/2012 | Dror .................. G21K 1/04 250/505.1 |
| 2013/0168567 A1 | 7/2013 | Wartski et al. |
| 2016/0192892 A1 | 7/2016 | Guez et al. |

OTHER PUBLICATIONS

Van Audenhaege, Karen et al., "Review of SPECT collimator selection, optimization, and fabrication for clinical and preclinical imaging", Aug. 2015, American Association of Physicists in Medicine, vol. 42, No. 8, pp. 4796-4813.

* cited by examiner

COLLIMATOR AND DETECTOR BASED MEDICAL IMAGING SYSTEMS

PRIORITY

This is a divisional of U.S. patent application Ser. No. 16/676,932 filed Nov. 7, 2019, which claims the benefits of U.S. Provisional Patent Application No. 62/758,183 filed Nov. 9, 2018 and U.S. Provisional Patent Application No. 62/760,659 filed Nov. 13, 2018, the entire disclosure of which is incorporated herein by reference.

BACKGROUND

In molecular medical imaging, sometimes known as nuclear medicine, images representing radiopharmaceutical distributions may be generated for medical diagnosis. Prior to imaging, radiopharmaceuticals are injected into an imaging subject such as a patient. The radiopharmaceuticals emit radioactive photons, which can penetrate through the body to be detected by a photon detector. Based on information from the received photons, the photon detector may then determine the distribution of the radiopharmaceuticals inside the patient. Their distribution represents the physiological function of the patient, and therefore images of their distribution provide valuable clinical information for diagnosis of a variety of diseases and conditions such as those in cardiology, oncology, neurology, etc.

A collimator is a device that guides photon path. In molecular imaging, photons may originate from unknown locations inside a subject, unlike in X-ray or CT where photons are emitted from a known source (or sources) position. Without collimators, photons from all directions may be recorded by gamma detectors, and image reconstruction may become difficult. Therefore, collimators are employed to guide possible photon paths so that images can be reconstructed, similar to the role of lens in a photography camera. Although existing collimator and detector imaging systems have been generally adequate for their intended purposes, they have not been entirely satisfactory in all respects. For example, existing imaging systems often have limited imaging sensitivity or resolution and often suffer from heavy noises. Therefore, improvements on collimator and detector imaging systems are desired.

SUMMARY

According to various embodiments, the present disclosure provides a medical imaging system, including a first collimator configured to filter radiation emitted from a subject, a first detector configured to detect radiation that has passed through the first collimator, a second collimator configured to filter radiation emitted from the subject, wherein the first collimator partially blocks a field of view (FOV) of the second collimator, and a second detector configured to detect radiation that has passed through the second collimator.

In some embodiments, the second detector and the second collimator are configured to move together. In some embodiments, the first collimator includes first openings for passing through radiation with a first aspect ratio of height to width, and the second collimator includes second openings for passing through radiation with a second aspect ratio of height to width. The first aspect ratio is higher than the second aspect ratio. In some embodiments, the first openings of the first collimator include parallel holes. In some embodiments, the second openings of the second collimator include multiple pinholes in a plate. In some embodiments, the number of the pinholes on the second collimator is 11 or greater. In some embodiments, the second collimator is positioned at least 3 cm away from the first collimator. In some embodiments, the first collimator is positioned on a peripheral of the FOV of the second collimator. In some embodiments, the first collimator includes a superior portion and an inferior portion which are separated by an empty portion, and the empty portion is outside a FOV of the first collimator but within the FOV of the second collimator. In some embodiments, the first collimator further includes left and right portions, each of which connects the superior and inferior portions. The left portion, the right portion, the superior portion, and the inferior portion together surround the empty portion. In some embodiments, a size of the first detector is such that the first detector is fully positioned between the first and second collimators. In some embodiments, the first detector is based on at least one of: cadmium telluride (CdTe), cadmium zinc telluride (CZT), and high purity germanium (HPGe). In some embodiments, the medical imaging system further includes an image processor configured to reconstruct a medical image of the subject based on radiation detected by both the first detector and the second detector, and a monitor configured to display the reconstructed medical image.

According to various embodiments, the present disclosure also provides a molecular breast imaging (MBI) system for examining a breast on a chest of a patient. The MBI system includes a first collimator configured for placement proximal to the chest, and a second collimator configured for placement distal to the chest. The first and second collimators are placed on a same side of the breast, and the second collimator is positioned further away from the breast than the first collimator. In some embodiments, the first and second collimators include first and second openings, respectively, for passing through radiation emitted from the patient. The first and second openings have first and second aspect ratios, respectively, of height to width, and the first aspect ratio is higher than the second aspect ratio. In some embodiments, the MBI system further includes a third collimator for placement proximal to the chest, and a fourth collimator for placement distal to the chest. The third collimator also includes openings for passing through radiation with the first aspect ratio of height to width, and the fourth collimator also includes openings for passing through radiation with the second aspect ratio of height to width. The third and fourth collimators are positioned on a same side of the breast that is opposite to the side of the breast where the first and second collimators are placed on. In some embodiments, the openings of the first collimator include parallel holes. In some embodiments, the openings of the second collimator include multiple pinholes. In some embodiments, the MBI system further includes a first detector configured to detect radiation that has passed through the first collimator, and a second detector configured to detect radiation that has passed through the second collimator. In some embodiments, the second collimator and the second detector are configured to move about the breast while maintaining a constant distance between the second collimator and the second detector.

According to various embodiments, the present disclosure also provides a method for examining a subject using molecular imaging. The method includes filtering, by a first collimator, photons emitted from the subject, detecting, by a first detector, photons that pass through the first collimator, filtering, by a second collimator, photons emitted from the subject, detecting, by a second detector, photons that pass through the second collimator, and reconstructing, by an image processor, a medical image of the subject based on photons detected by both the first and second detectors. In some embodiments, the first and second collimators are positioned such that their fields of view partially overlap in an overlapping region. In some embodiments, the reconstructing of the medical image includes reconstructing a first partial image based on photons that pass through the overlapping region and are detected by the first detector, and reconstructing a second partial image based on photons detected by the second detector. The reconstruction of the second partial image uses the first partial image as an initial estimate for the overlapping volume. In some embodiments, the reconstruction of the second partial image further updates the first partial image using an iterative method.

BRIEF DESCRIPTION OF THE DRAWINGS

The present disclosure is best understood from the following detailed description when read with the accompanying figures. It is emphasized that, in accordance with the standard practice in the industry, various features are not drawn to scale and are used for illustration purposes only. In fact, the dimensions of the various features may be arbitrarily increased or reduced for clarity of discussion.

DETAILED DESCRIPTION

The following disclosure provides many different embodiments, or examples, for implementing different features of the disclosure. Specific examples of components and arrangements are described below to simplify the present disclosure. These are, of course, merely examples and are not intended to be limiting. Any alterations and further modifications to the described devices, systems, methods, and any further application of the principles of the present disclosure are fully contemplated as would normally occur to one having ordinary skill in the art to which the disclosure relates. For example, the features, components, and/or steps described with respect to one embodiment may be combined with the features, components, and/or steps described with respect to other embodiments of the present disclosure to form yet another embodiment of a device, system, or method according to the present disclosure even though such a combination is not explicitly shown. In addition, the present disclosure may repeat reference numerals and/or letters in the various examples. This repetition is for simplicity and clarity and does not in itself dictate a relationship between the various embodiments and/or configurations discussed.

Moreover, a feature on, connected to, and/or coupled to another feature in the present disclosure that follows may include embodiments in which the features are in direct contact, and may also include embodiments in which additional features may interpose the features, such that the features may not be in direct contact. In addition, spatially relative terms, for example, "lower," "upper," "horizontal," "vertical," "above," "over," "below," "beneath," "up," "down," "top," "bottom," etc., as well as derivatives thereof (e.g., "horizontally," "downwardly," "upwardly," etc.) are used for ease of the present disclosure of one features relationship to another feature. The spatially relative terms are intended to cover different orientations of the device including the features. Still further, when a number or a range of numbers is described with "about," "approximate," and the like, the term is intended to encompass numbers that are within a reasonable range including the number described, such as within +/−10% of the number described or other values as understood by person skilled in the art. For example, the term "about 5 cm" encompasses the dimension range from 4.5 cm to 5.5 cm.

The present disclosure is generally related to the field of medical imaging, and more particularly to the design of collimator and detector used in molecular imaging systems.

In molecular medical imaging systems, collimator and detector work in tandem to generate images that represent radiopharmaceutical distributions within a subject. However, existing collimator and detector designs suffer from various issues. For example, conventionally only one type of collimator is used to guide photons, but one collimator type is often insufficient to capture enough useful photons emitted from a patient, which leads to limited imaging sensitivity or resolution. For another example, sometimes a collimator-based imaging system is used to image a certain part of a patient, such as a breast. In this case, to increase imaging sensitivity, the collimator often has holes or other pass-through features that allow wide angles of incident photons to pass through. But with such a design, the collimator may also allow undesired photons (photons emitted from other parts of the patient's body) to pass through, thereby increasing noise.

The present disclosure provides new collimator and detector system designs to solve the problems in conventional systems and to improve performance. According to some embodiments, a molecular imaging system uses multiple types of collimators and detectors (instead of a single collimator type and a single detector type) on the same imager head (positioned at the same side of a patient). In an example system, a first collimator is configured to filter radiation emitted from a subject, and a first detector is coupled to (e.g., fixed to or movably connected to) the first collimator to detect radiation that has passed through the first collimator. A second collimator, which is of a type different from the first collimator, is positioned on the same side of the subject as the first collimator but further away from the subject than the first collimator and configured to filter radiation emitted from the subject, and a second detector is coupled to (e.g., fixed to or movably connected to) the second collimator to detect radiation that has passed through the second collimator. The first collimator may be disposed on the peripheral of a field of view (FOV) of the second collimator. As a result, the first collimator partially restricts or blocks the FOV of the second collimator, but its empty center portion allows the second collimator to receive photons therethrough. Such a configuration allows the first collimator and detector tandem to pick up peripheral photons, which increases imaging sensitivity, while reducing noises to be received by the second collimator. Therefore, system performance may be improved.

Figure 1A:
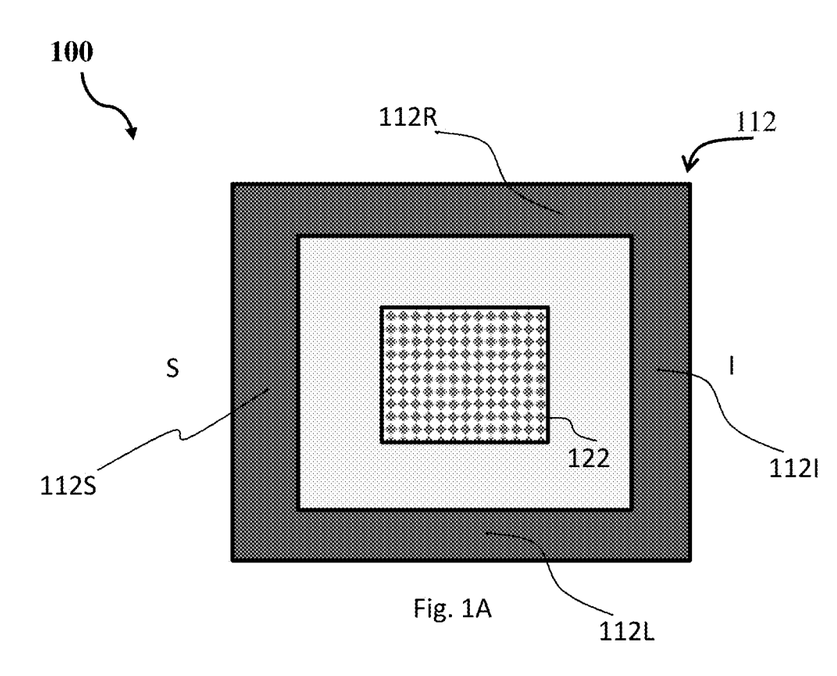
FIGS. 1A and 1B are schematic top and cross-sectional views, respectively, of an example imaging system according to various aspects of the present disclosure.
Figure 1B:
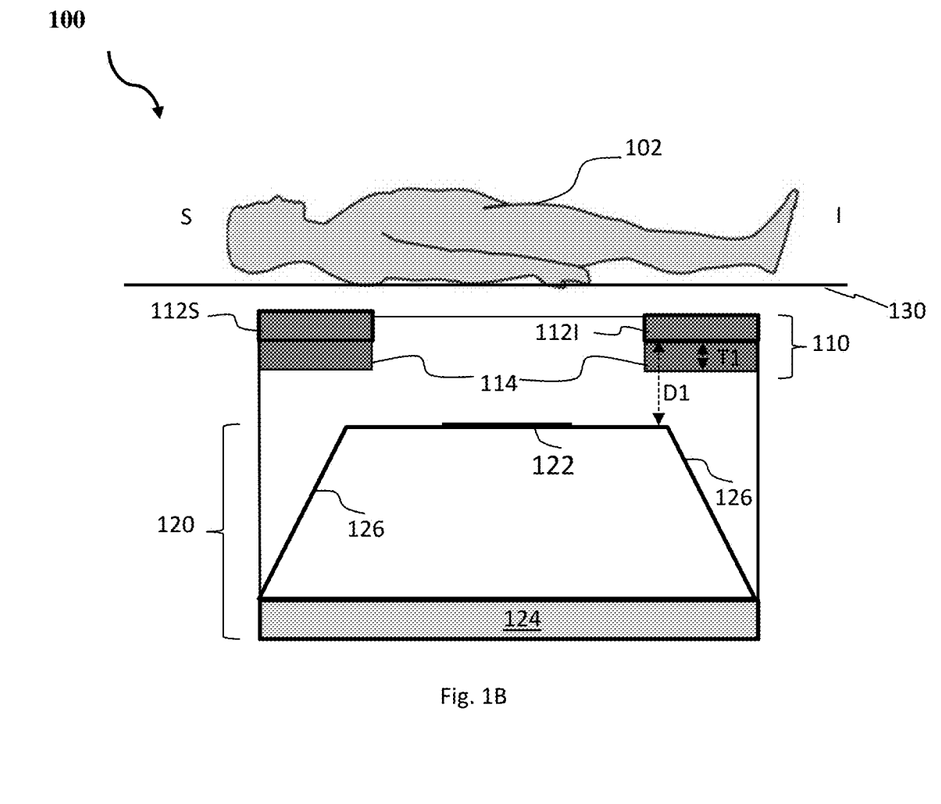

FIGS. 1A and 1B are schematic top and cross-sectional views, respectively, of an example imaging system 100, which may be used to medically examine or treat a subject such as patient 102. Imaging system 100 is a hybrid system including two imaging modules or parts (called imagers herein) 110 and 120. Imager 110 includes first collimator 112 and first detector 114, and imager 120 includes second collimator 122 and second detector 124. Imaging system 100 may include other parts such as connectors that couple parts together (e.g., connecting imagers 110 and 120 together), motors that cause parts to move, photon shielding components, a housing component that contains other parts, etc. For example, a coupling and shielding component 126 may connect collimator 122 and detector 124 such that collimator 122 and detector 124 move (e.g., rotate) together, and prevent radiation (photons) from reaching detector 124 through paths other than collimator 122. In other embodiments, collimator 122 and detector 124 may move individually with respect to each other. Notations "S" and "I" in FIGS. 1A and 1B stand for superior (head) and inferior (foot) positions, respectively.

When imaging system 100 is used to medically examine or treat patient 102, which may be a human or an animal, one or more radiopharmaceuticals may be taken orally or injected into patient 102. The radiopharmaceutical undergoes nuclear decay and may emit, either directly or indirectly through annihilation, radiation (e.g., gamma photons) at certain rate(s) and with characteristic energies. Detectors 114 and 124 are placed near patient 102 to record or monitor emissions. In some embodiments, detectors 114 and 124 are organized in planar shapes to acquire data in a two-dimensional (2D) matrix format, which may be called projections. In other embodiments, detectors 114 and 124 have curved surface shapes to increase a surface area for receiving photons with incident angles greater than zero. Based on recorded information such as position, energy, and counts of such detected events, an image of radiopharmaceutical distribution may be reconstructed to study the status or function of certain body parts on patient 102.

Figure 2:
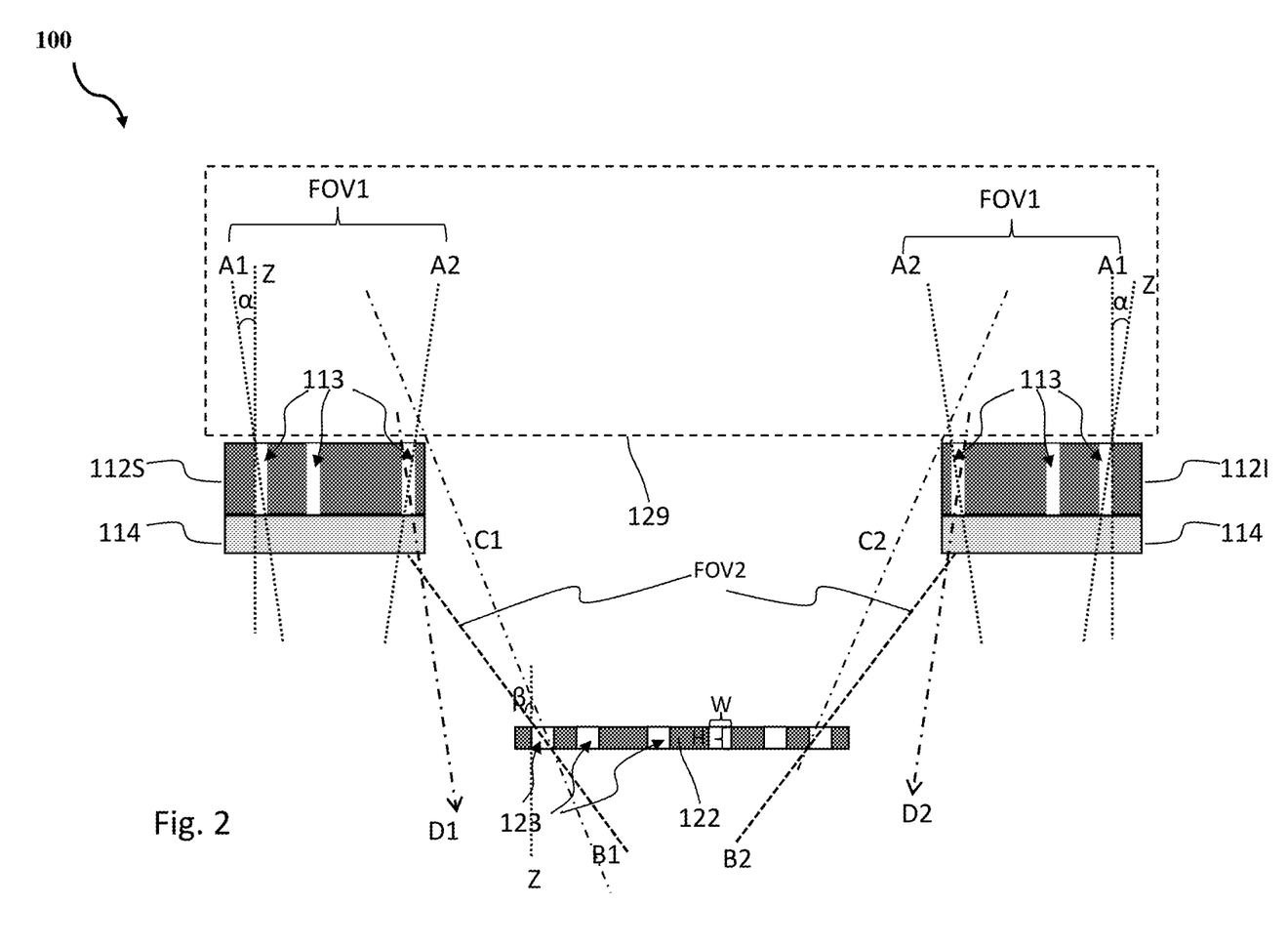
FIG. 2 is a schematic cross-sectional view of part of an imaging system according to various aspects of the present disclosure.

FIG. 2 is a schematic cross-sectional view of part of imaging system 100. In an embodiment, collimator 112 is configured to filter radiation emitted from patient 102, and detector 114 is coupled to collimator 112 to detect radiation that has passed through collimator 112. Collimator 122 is positioned further away from patient 102 than collimator 112 and configured to filter radiation emitted from patient 102. As an example, collimator 122 may be placed at least several centimeters (e.g., 5 cm) away from a resting platform 130 for patient 102, while collimator 112 may be placed as close as possible to the resting platform 130 for patient 102 (e.g., 2 cm or less, such as a few millimeters). Thus, collimator 122 is placed below collimator 112 at a certain distance (e.g., at least 3 cm, or 5 cm, or 10 cm, or 15 cm, or 30 cm, or between 1 to 2 meters, or greater than 2 meters), where different distances may suit different applications or purposes. The distance between collimator 112 and collimator 122 is needed for optimizing performance of collimator 122 such as improving resolution. The distance between patient 102 and collimator 122 may also depend on the types of openings on collimators 112 and 122, which are described further below. Detector 124 is coupled to collimator 122 to detect radiation that has passed through collimator 122. Collimator 112 may be empty in its center portion and may be disposed along the perimeter of an FOV of collimator 122. As a result, collimator 112 partially blocks the FOV of collimator 122, but its empty center portion allows collimator 122 to receive photons therethrough. Such a configuration allows collimator 112 and detector 114 to pick up peripheral photons, which makes good use of the space and increases imaging sensitivity, while reducing noises to be received by collimator 122. Therefore, system performance may be improved. In an alternative embodiment, the center portion of collimator 112 is not empty but nonetheless transparent to the radiation emitted from patient 102. This achieves the same or similar effects as having an empty center portion.

Collimators 112 and 122 are configured to filter radiation by blocking certain photons and passing through other photons. Collimators 112 and 122 may each be made of one or more radiation (e.g., photons) absorbing heavy medal(s), such as lead and/or tungsten. Collimator 112 has openings 113 built therein to allow some photons to pass through, and collimator 122 has openings 123 built therein to allow some photons to pass through. It should be understood that radiation or photon blocking or absorption by collimators disclosed herein does not require blocking of 100% of photons because a small percentage of photons (e.g., 5% or less) may still penetrate through the full thickness of the radiation absorbing material. The number of escaping photons may decrease exponentially with the thickness of a collimator. In other words, blocking (or other similar terms) means that substantially all of the photons (e.g., 95% or more, or 98% or more) are absorbed by the radiation absorbing material.

As shown in FIG. 2, a photon may hit a top surface of collimator 112 with an acceptable incident angle (denoted by symbol α in FIG. 2 as an angle between line A1 and the vertical direction Z where line A1 is the travel direction of the photon and direction Z is the normal of the top surface of collimator 112). If the incident angle is greater than a predetermined threshold value, the photon would be absorbed by collimator 112 (note there are occasions where the photon cuts through a portion of collimator 112 adjacent the opening (e.g., a thin area on the sidewall of the opening)). Therefore, the acceptable incident angle α represents the range of possible incident angles for photons to pass through an opening 113 without cutting through a portion of collimator 112.

In some embodiments, this threshold value ranges from 0° to about 2° or from 0° to about 10°. In an example, a LEHR (low energy high resolution) collimator has an opening diameter of about 1.11 mm and a length of about 24.04 mm, with an acceptable incident angle range of 0° to about 2.64°. In another example, a GAP (general all purpose) collimator has an opening diameter of about 1.40 mm and a length of about 25.4 mm, with an acceptable incident angle range of 0° to about 3.15°). In yet another example, a LEHS (low energy high sensitivity) collimator has an opening diameter of about 2.54 mm, a length of about 24.04 mm, with an acceptable incident angle range of 0° to about 6.03°. The acceptable incident angle for collimator 112 is often less than 10°. Photons that can pass through collimator 112 is considered within an FOV of collimator 112 (denoted in FIG. 2 as FOV1, which is a space within lines A1 and A2).

Similarly, for collimator 122, if a photon hits a top surface of collimator 122 with an incident angle (denoted by symbol β in FIG. 2 and defined as the travel direction of the photon and the normal of the collimator 122) greater than a predetermined threshold value, the photon would be absorbed by collimator 122 (note there are occasions where the photon cuts through a portion of collimator 122 adjacent the opening (e.g., a thin area on the sidewall of the opening)). So only photons incident on the surface of an opening 123 with incident angles less than the threshold value can possibly pass through opening 123. In some embodiments, this threshold value ranges from 0° to about 15°, or 0° to about to 75°. For example, an opening with a diameter of about 1.0 mm and a length of about 3.0 mm has an acceptable incident angle of about 18.43°, and an opening with a diameter of about 3.0 mm and a length of about 1.5 mm has an acceptable incident angle of about 63.43°. The acceptable incident angle for collimator 122 is greater than that for collimator 112 (e.g., greater than 15°). Photons that can pass through collimator 122 is considered within an FOV of collimator 122 (denoted in FIG. 2 as FOV2, which is a space within lines B1 and B2). In some embodiments, openings 113 and/or 123 have irregular shapes. For example, an opening 113 may have a different width from another opening 113, and an opening 123 may have a different width from another opening 123. An opening 113 or 123 itself may have a varying width. In such cases, the incident angle (α or β) may be determined using flexible methods that are consistent with principles disclosed herein (i.e., the goal is for collimator 112 to pass photons that have a narrower range of incident angles than collimator 122).

In some embodiments, openings 113 on collimator 112 are configured to pass through radiation within a relatively narrow range of incident angles (e.g., a is between 0 to about 10 degrees), while openings 123 on collimator 122 are configured to pass through radiation within a wider range of incident angles (e.g., β is between 0 to about 30 degrees, or between 0 to about 75 degrees). In some embodiments, the acceptable incident angle for collimator 122 is at least twice the acceptable incident angle for collimator 112. In an embodiment, the acceptable incident angle for collimator 122 is at least three times of the acceptable incident angle for collimator 112. In other words, FOV1 may be designed to be narrower than FOV2. The allowable pass-through angles of radiation may be controlled by tailoring various parameters such as length, size, shape, and tilt orientation of each opening 113 or 123. In an embodiment, collimator 112 has openings with higher aspect ratios (hole length over diameter or width) than collimator 122. For example, at least some openings 113 may have a higher aspect ratio of height to width than some openings 123. The aspect ratio may be determined using any suitable methods. As shown in FIG. 2, the aspect ratio of an opening 123 may represent a ratio between a height (denoted as H) of opening 123 and a width (denoted as W) of opening 123. In some embodiments, openings 113 and/or 123 have irregular shapes. For example, an opening 113 may have a different width from another opening 113, and an opening 123 may have a different width from another opening 123. An opening 113 or 123 itself may have a varying width. In such cases, the aspect ratio may be determined using flexible methods that are consistent with principles disclosed herein (i.e., the goal is for collimator 112 to pass photons that have a narrower range of incident angles than collimator 122). Such a goal may be achieved, for example, if openings 113 are smaller and/or deeper than openings 123. In some embodiments, patient 102 is positioned within a target volume 129 of imaging system 100, as illustrated in FIG. 2. Target volume 129 is shown as a rectangle box in the cross-sectional view of FIG. 2, but in a 3D view may take the form of a cylinder. For example, the target volume may be a cylinder with a diameter of 50 to 70 cm. The target volume for specific body parts such as head might be smaller. In such cases, the design consideration for openings 113 and 123 applies to some openings 113 whose FOVs overlap with some FOVs of openings 123 within target volume 129. Because the FOVs of openings 113 and 123 grow wider when moving upward farther away from openings 113 and 123, the concept of FOV overlapping specifically applies within target volume 129.

Openings 113 and 123—which may also be called tunnels, apertures, or pass-through features—may have any suitable shape, size, number, and/or distribution within their respective collimators. In some embodiments, openings 113 may include parallel holes, fan beams, cone beams, slit-slat, pinholes, multi-pinholes, any other suitably shaped openings, or combinations thereof. In some embodiments, collimator 112 is placed very close (e.g., 2 cm or less) to patient 102. Thus, collimator 112 may use parallel holes or fan-beams (converging or diverging) since such features do not need significant separation from patient 102. In some embodiments, openings 113 may slant, converge, or diverge and may form fan beams or cone beams, etc. Openings 123 may include parallel holes, fan beams, pinholes, multi-pinholes, any other suitably shaped openings, or combinations thereof. In an example, openings 123 include a plurality of pinholes, where the number of pinholes may be greater than 11, greater than 23, or greater than 59, or greater than 100. For example, a commonly used coded aperture pattern, MURA (modified uniformly redundant array) of sizes 5, 7, 11, and 13 comprise 12, 24, 60, and 84 holes, respectively. A higher number of pinholes helps improve imaging sensitivity. Further, openings 123 may be single pinhole, multi-pinhole, multiple pinhole modules (including spread field imaging (SFI) or coded aperture). In some embodiments, openings 123 may slant, converge, or diverge and may form fan beams or cone beams, etc. In an embodiment, openings 113 and 123 have different shapes (e.g., openings 113 being parallel holes, while openings 123 being multi-pinholes).

In some embodiments, collimators 112 and 122 are each made of narrow openings separated by walls made of heavy metal called septum. As shown in FIG. 2, collimators 112 and 122 each include a perforated plate made of heavy metal such as lead and tungsten. The thickness of the plate, depending on the energy of photons imaging system 100 is designed to image, is large enough to stop the majority of the radiation so that photons primarily pass through the openings on the plate. For example, for the commonly used isotope, Technetium-99m ($^{99m}$Tc), emitting gamma rays with energy around 140 keV, a thickness of 2 mm to 3 mm is usually enough for a plate made of lead, and a thickness of 1.5 mm to 2 mm for tungsten. The thickness may be greater to image higher energy gamma rays. Photons pass through the openings in the collimator plate. Sometimes, the height of an opening, i.e., the thickness of the collimator, is much larger than the opening width. For example, an opening width may be 2-3 mm, while an opening height may be greater than 2 cm. Collimators 112 and 122 may be placed at certain distances from their respective detectors to allow photons coming from the designed FOV passing the openings to spread across the detector surface. In some embodiments, collimator 112 is placed very close to detector 114, e.g., with no gap or with a gap equal to or less than about 2 cm. In comparison, collimator 122 is placed relatively far away from detector 124, e.g., with a gap of about 3 cm or greater, often more than 5 cm. The distance between the bottom surface of collimator 122 and a top surface of detector 124 is large enough that photons pass through neighboring openings may be received by the same overlapping area on detector 124 (or some areas of detector 124 may receive photons passing through different openings). This is an effect often called photon multiplexing. In an example, a distance between the bottom surface of collimator 122 and a top surface of detector 124 is at least half of a distance between patient 102 and the top surface of collimator 122.

In some embodiments, collimator 112 is coupled to detector 114 such that they move (e.g., rotate) together. In other embodiments, collimator 112 and detector 114 may move individually with respect to each other. Similarly, collimator 122 and detector 124 may move together or individually with respect to each other. Further, imager 110 and imager 120 may be configured to move together or individually with respect to each other. In an example, imager 110, or imager 120, or both may move during imaging while patient 102 remains still. Imager 120 may move while imager 110 remains still, or vice versa. The motion of an imager (e.g., imager 110 or 120) may include shifting laterally (in x or y directions), or shifting vertically (in z direction), or tilting, or rotating, or combinations thereof. In some embodiments, when an imager moves, images are captured in a "step and shoot" fashion including, for example, the following operations: moving the imager to a first position, acquiring a first image from the first position for a period of time, moving the imager to a second position, and acquiring a second image from the second position for a certain period of time. The imagers may move about patient 102 to other positions to repeat the operations.

Collimator 112 may have various suitable shapes and dimensions. As shown in the top view of FIG. 1A, in this embodiment, collimator 112 has four arms or portions including superior portion 112S, inferior portion 112I, left portion 112L, and right portion 112R, which together surround an empty center portion. Superior portion 112S and inferior portion 112I of collimator 112 correspond to the superior and inferior sides of patient 102, respectively. Superior portion 112S and inferior portion 112I are separated by the empty center portion, which allows radiation to reach collimator 122. Although FIG. 1A illustrates collimator 112 as having four portions located along the peripheral of an FOV of collimator 122), collimator 112 may take any suitable configurations in various embodiments. In an embodiment, collimator 112 may be of one continuous piece that fully surrounds the peripheral of the FOV of collimator 122. In another embodiment, collimator 112 may include discrete (or disjoint) portions that are located along the peripheral of the FOV of collimator 122. To further this embodiment, collimator 112 may have any suitable number of portions or sides such as one side, two sides, three sides, four sides, or more than four sides. For example, collimator 112 may include one or more of the superior portion 112S, inferior portion 112I, left portion 112L, and right portion 112R. Note that the orientations (superior, inferior, left, and right) are used herein to represent the four sides of collimator 112. The relative position with regard to a subject may change as the camera/collimator module rotates around the subject. In medical imaging, as patients usually have bigger length (height) than width, in some embodiments, collimator 112 may include only two portions, which usually are portions 112S and 112I. Each portion of collimator 112 may have a regular shape or an irregular shape and may have curved or straight edges. Further, the discrete portions of collimator 112 may be placed at any appropriate locations along the peripheral of the FOV of collimator 122. For example, the portions 112S and 112I may be placed proximate to the head and foot of the subject, while the portions 112L and 112R may be placed proximate the left and right sides of the subject, or proximate the front and back sides of the subject. Still further, the portions 112L and 112R may be placed symmetrically or asymmetrically with respect to a centerline from the head to the foot of the subject.

Collimator 112 is coupled to one or more detectors 114, which may record photon counts for imaging. Information collected by detector 114 increases imaging sensitivity because photons from more areas are detected than using detector 124 alone. The overall size of imager 110 fits in a space between patient 102 and imager 120. Within imager 110, detector 114 may have any suitable size that allows it to fit in a space between collimators 112 and 122. In an embodiment, detector 114 has a relatively compact size or small footprint such that its thickness (denoted as T1 in FIG. 1B) is less than a distance between a bottom surface collimator 112 and a top surface of collimator 122, and that its width is not greater than a width of collimator 112 (that is, in a top view such as FIG. 1A, detector 114 is hidden underneath collimator 112). The compact size helps reduce costs and/or system size. In some embodiments, detector 114 is a direct conversion detector that converts X- or gamma ray photons directly into electrical signals. One type of such direct conversion detectors is semiconductor detector (i.e., a semiconductor-based detector), such as one based on cadmium telluride (CdTe), cadmium zinc telluride (CZT), or high purity germanium (HPGe). Collimator 112 may also be a scintillator coupled with compact photo multiplier tubes (PMTs), silicon photomultiplier tubes (SiPMT), or avalanche photodiodes. Each portion or side of collimator 112 may be associated with (or coupled to) a dedicated detector 114. Alternatively, multiple portions of collimators 112 may share a detector 114. On the other hand, within imager 120, detector 124 may be of a different type than detector 114. In an embodiment, detector 124 is a scintillator (such as sodium iodide (NaI) or caesium iodide (CsI) based) detector.

In addition to filtering detecting photons, imager 110 (including collimator 112 and detector 114) may serve other purposes. For example, imager 110 acts as an FOV limiter, which limits the area that can be seen by collimator 122. As shown in FIG. 2, the FOV of collimator 112 (FOV1 within lines A1 and A2) overlaps with the FOV of collimator 122 (FOV2 within lines B1 and B2) in an overlapping volume or region. In other words, if lines A1, A2, B1, and B2 are extended upwards, lines A1 and B1 would intercept each other over the left side of collimator 112, and lines A2 and B2 would intercept each other over the right side of collimator 112). In an embodiment, imager 110 is disposed on the peripheral of FOV2 such that imager 110 partially blocks FOV2. For example, imager 110 may partially block the FOV of one or more openings 123 that are disposed closest to imager 110. As illustrated in FIG. 2, superior portion 112S of imager 110 blocks the volume of space between lines B1 and C1 from the left-most opening 123 on collimator 122, where line C1 connects the top-right corner of superior portion 112S and the bottom-right corner of the left-most opening 123 on collimator 122. Similarly, inferior portion 112I of imager 110 blocks the volume of space between lines B2 and C2 from the right-most opening 123 on collimator 122, where line C2 connects the top-left corner of inferior portion 112I and the bottom-left corner of the right-most opening 123 on collimator 122. On the other hand, to allow photons to reach collimator 122, the empty portion of collimator 112 is outside FOV1 but within FOV2. In that sense, imager 110 serves as a view finder for imager 120. Because openings 123 have wider acceptable incident angles than openings 113, line C1 would intercept line A1 if extended far enough. In some embodiments, even the FOV of the leftmost opening 113 in collimator portion 112S (or the rightmost opening 113 in collimator portion 112I, as shown in FIG. 2) partially overlaps with the FOV of collimator 122 within target volume 129. Further, collimator 122 may not be in FOV1. Thus, photons that have passed through openings 113 in collimator 112 do not pass through openings 123 in collimator 122. For example, as shown in FIG. 2, a photon travelling along line D1 or line D2 (after passing through an opening 113) may not pass any opening 123. Such a configuration allows collimators 122 and/or 112 to have a smaller footprint (e.g., width and/or length) than conventional collimators, thereby reducing system cost. One design is to mix high-cost and low-cost detectors for collimators 112 and 122 to subsequently reduce the overall cost of imaging system 100. In one example, detector 114 is a high-cost, high-performance detector such as semiconductor-based detectors (e.g., CZT detector), and detector 124 is a scintillator-based detector, or vice versa. In this case, the overall cost of detectors 114 and 124 is lower than the cost of using CZT detectors for both detectors 114 and 124.

The imaging modality used by imaging system 100 may include gamma camera, SPECT (single photon emission computed tomography), and PET (positron emission tomography), and other suitable ones. In SPECT imaging, for instance, one or more collimators 112 is placed between detector 114 and patient 102, and openings 113 on collimator 112 may determine the directions and angular span from which radiation can pass through collimator 112 to reach a certain position on detector 114. Similarly, one or more collimators 122 may be placed between detector 124 and patient 102, and openings 123 on collimator 122 may determine the directions and angular span from which radiation can pass through collimator 122 to reach a certain position on detector 124. In some embodiments, collimator 122 and detector 124 are connected or fixed together via coupling component 126, which also provides shielding to prevent photons passing through the space between 122 and 124. In SPECT imaging, cameras may be rotated to acquire 2D images from different angles. In an embodiment, collimator 122 and detector 124 may move (e.g., rotate) together. Parts 110 and 120 may also be connected so that they rotate together to acquire images.

Data acquired from imager 110 can be used to reconstruct an image of FOV1 independently. Further, data from sub-parts of imager 110 (e.g., collimator portions 112S, 112I, 112L, or 112R) may be reconstructed independently as well. Various methods including filtered back projection, algebraic, or statistical methods (such as an expectation and maximization (EM) method or an ordered subset expectation maximization (OSEM) method) may be used for image reconstruction with a parallel collimator. In some embodiments, image signals (sometimes called counts) from both imager 110 and imager 120 can be used together in image reconstruction. For instance, data acquired from imager 120 can be used to reconstruct an image of FOV2 using an iterative method. The iterative method utilizes image data reconstructed in FOV1 from imager 110 as an initial guess for the overlapping volume of FOV1 and FOV2. In some embodiments, signal(s) from imager 110 can be reconstructed to generate a cross-sectional image of FOV1 (denoted as F1), which may have relatively low resolution. Because FOV1 and FOV2 overlap, part of the reconstructed image F1 that represents a region overlapping with FOV2 may be used as initial estimate for reconstruction of the overlapping region. The overlapping region may be updated sequentially with image reconstruction using data from imager 110 and from imager 120. Alternatively, the overlapping region may be updated simultaneously with image reconstruction using data from images 110 and 120 together.

Figure 3:
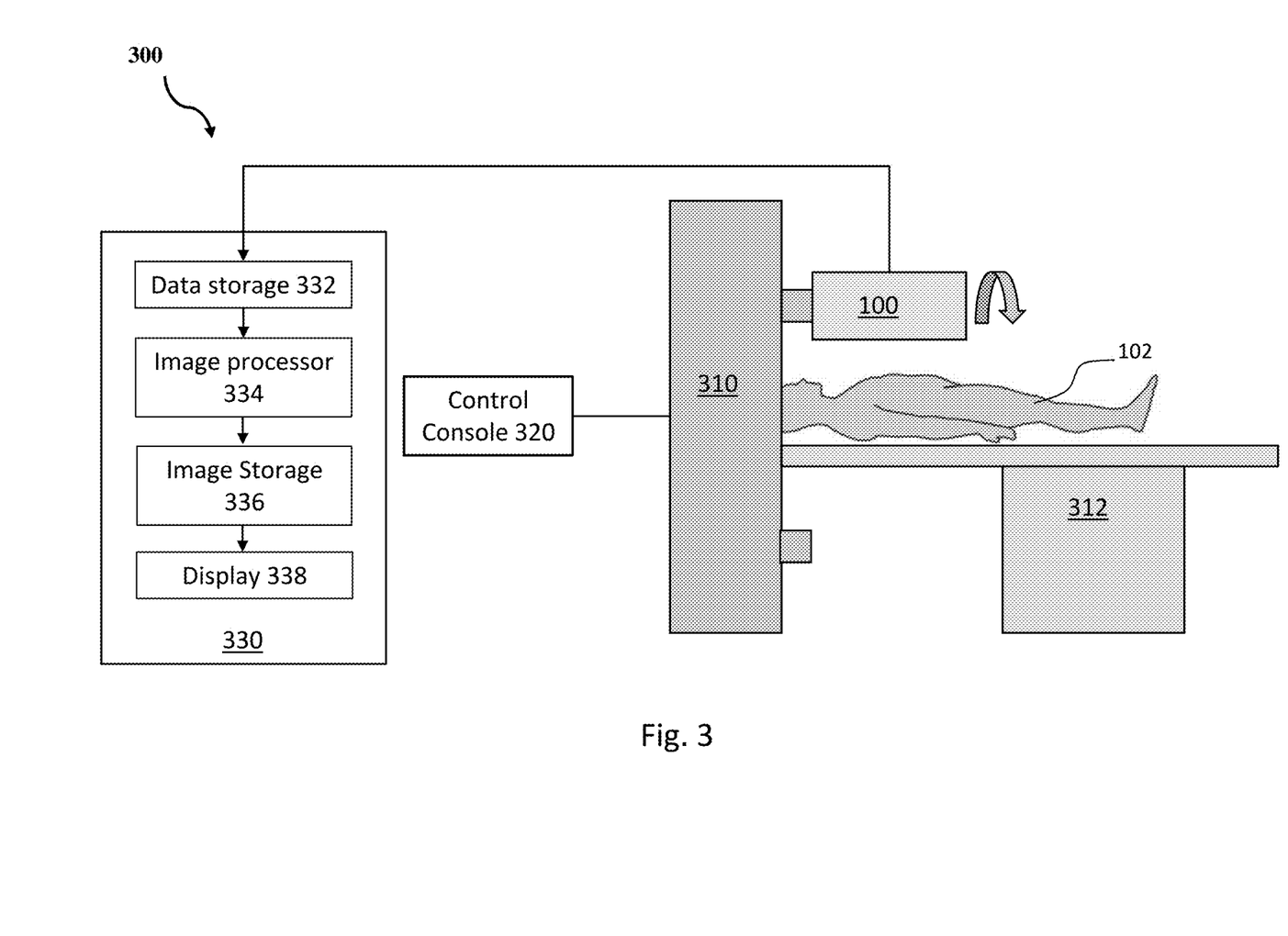
FIG. 3 is a schematic diagram of an example nuclear imaging system according to various aspects of the present disclosure.

Image reconstruction may use system 100 and other systems or components coupled therewith. FIG. 3 illustrates an example molecular or nuclear imaging system 300, which includes imaging system 100, a gantry 310, a platform 312, a control console 320, and a computer system 330. In the present embodiment, computer system 330 includes a data storage unit 332, an image processor 334, an image storage unit 336, and a display 338. One or more imaging modules (e.g., imaging system 100 including imagers 110 and/or 120) are mounted on gantry 310, which may move, rotate, and acquire data simultaneously. Patient 102 is placed on a platform 312 (e.g., a couch) for examination or treatment by imaging system 100. In some embodiments, imagers 110 and/or 120 are coupled to gantry 310 through movable parts so that they may move (e.g., rotate) on gantry 310.

Imagers 110 and/or 120 may detect and record radiation emitted from patient 102 and transfer recorded information to data storage unit 332. Then, image processor 334 may use the recorded information to reconstruct volumetric images representing radiopharmaceutical distributions within patient 102. The reconstructed images are stored in the image storage unit 336, which can be manipulated and displayed on display 338 for viewing. Control console 320 may be used by an operator or technician to control imaging system 100 in acquiring data. In some embodiments, control console 320, data storage unit 332, image processor 334, image storage unit 336, and display 338 are integrated in a computer system 330. In some embodiments, one or more computer components (such as control console 320, data storage unit 332, image processor 334, image storage unit 336, and display 338) can be partially or entirely located at a remote location (e.g., on the cloud). In some embodiments, one of more of these components may exist locally or remotely.

The present disclosure provides distinctive methods for nuclear medicine and molecular imaging to accommodate a collimator such as collimator 122, which may have a plurality of pinholes (called a multi-pinhole collimator). Image reconstruction methods may use equations (1), (2), (2-1), and (2-2), described below. An example method in image reconstruction is called a maximum likelihood expectation and maximization (MLEM) method, which estimates object images using equation:

$$\hat{f}_j^{(k+1)} = \frac{\hat{f}_k^{(k)}}{\sum_{i=1}^{I} K_{ij}} \sum_{i=1}^{I} \frac{p_i K_{ij}}{\sum_{j=1}^{J} K_{ij}\hat{f}_j^{(k)}} \quad (1)$$

where $\hat{f}_j^{(k+1)}$ is the (k+1)th estimate of the jth element of f, the object image, $p_i$ is the ith element of a measured image, and $K_{ij}$ is a transition matrix representing the probability of photon emitted from jth element of the object being detected by the ith element of a detector. Let $p_r$ be the denominator inside the second summation: $p_r = \sum_{j=1}^{J} K_{ij}\hat{f}_j^{(k)}$, often called a forward projection representing an expectation of measured image based on the kth estimated object image $\hat{f}^{(k)}$.

In some cases such as when a coded aperture mask is used as a collimator, equation (1) can be further written as $$\hat{f}^{(k+1)} = \hat{f}^{(k)} \times \left( h \otimes \frac{p_c}{\hat{f}^{(k)} * h} \right) \quad (2)$$

where h is a coded aperture mask shadow, and $p_c$ is a measured image after correction for angular effects. $p_c = p * Cc$, where Cc is the angular effect correction factor, and $*$ and $\otimes$ represent convolution and correlation operations. The coded aperture mask is a plate (made of heavy metal such as lead and tungsten) with multiple pinholes. Representing the mask, h is a matrix. In the original form, h is a matrix of "0"s and "1"s, where each element corresponds to a grid position on the plate, 1 represents an opening (pinhole) at that position, and 0 represents otherwise. This matrix can be magnified to represent the magnifying effect of the mask shadow projected by a source on the detector, and interpolation may be used to calculate the matrix element values.

Equation (2) is suitable for a thin imaging subject whose thickness is much smaller than the distance between the subject and a collimator such as collimator 122. For thicker subjects, a three-dimensional (3D) method is used. For example, a subject image at distance z can be estimated using the following equation:

$$\hat{f}^{(K+1)}(z) = \frac{\hat{f}^{(K)}(z)}{\sum_{x,y} h(z)} \left[ h(z) \otimes \frac{p_c - \sum_{z \neq z'} \hat{f}^{(K)}(z') * h(z')}{\hat{f}^{(K)}(z) * h(z)} \right] \quad (2\text{-}1)$$

A slightly different formula can be used to estimate the subject as well:

$$\hat{f}^{(K+1)}(z) = \frac{\hat{f}^{(K)}(z)}{\sum_{x,y} h(z)} \left[ h(z) \otimes \frac{p_c}{\sum_z \hat{f}^{(K)}(z) * h(z)} \right] \quad (2\text{-}2)$$

Figures 4A, 4B:
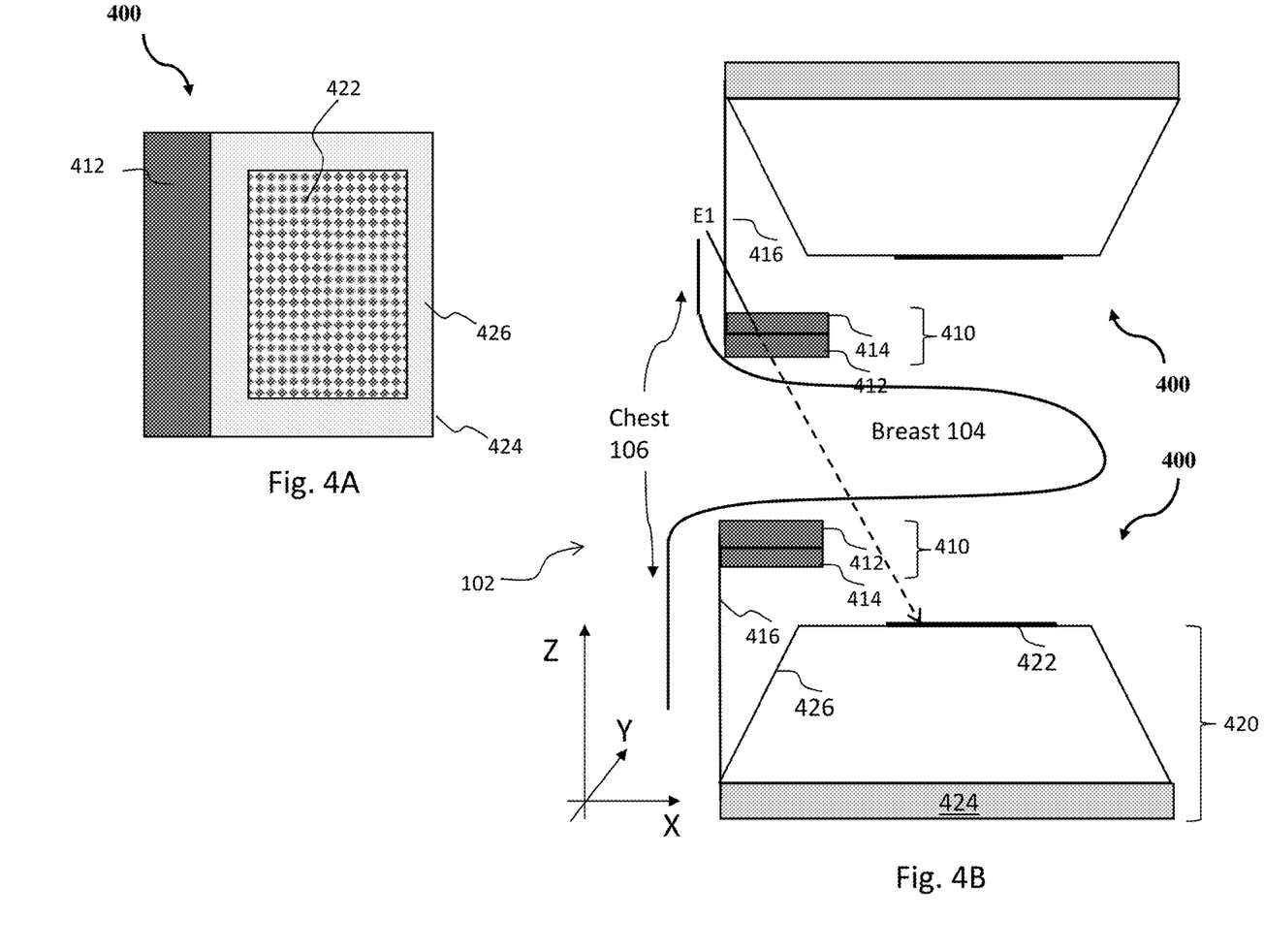
FIG. 4A is a schematic top view of one molecular breast imaging (MBI) system.
FIG. 4B is a cross-sectional view of two MBI systems shown in FIG. 4A, according to various aspects of the present disclosure.

The present disclosure provides imaging techniques that, depending on the application, may be used for general purpose imaging or for imaging certain body parts of a subject such as patient 102. For example, systems disclosed herein may be used for the imaging of human breast(s). FIGS. 4A and 4B illustrate an example molecular breast imaging (MBI) system 400, which may be designed to acquire images of a breast 104 (located on the chest 106 of patient 102) for screening or diagnosis of diseases such as breast cancer. Specifically, FIG. 4A is a schematic top view of one MBI system 400, and FIG. 4B is a cross-sectional view of two MBI system 400s, each deployed on a different side of breast 104 (e.g., one underneath breast 104, and another above breast 104). In some embodiments, each MBI system 400 in FIG. 4B may be considered an imaging unit of the overall (bigger) MBI system shown in FIG. 4B. In practice, depending on factors such as costs, one or more such imaging units may be used on breast 104. In the interest of clarity, the following descriptions focus on one MBI system 400, with the understanding that similar principles may be used for the other MBI system 400 (note, however, that differences may exist between two MBI systems used on different sides of breast 104).

In the embodiment shown in FIGS. 4A and 4B, each imaging system 400 is a hybrid system including two imaging modules or parts (called imagers) 410 and 420. Imager 410 includes first collimator 412 and first detector 414, and imager 420 includes second collimator 422, second detector 424. Imaging system 400 may include other parts such as connectors that couple parts together, motors that cause parts to move, photon shielding components, a housing component that contains other parts, etc. For example, a coupling and shielding component 426 may connect collimator 422 and detector 424 such that collimator 422 and detector 424 move (e.g., rotate) together, and also provide shielding around imager 420. Since one skilled in the art would recognize that various aspects of MBI system 400 are similar to imaging system 100 and that various characteristics of imaging system 100 would similarly apply to counterparts in MBI system 400, such similar aspects are not repeated below in the interest of conciseness. On the other hand, various characteristics of MBI system 400 can also be used in imaging system 100 where applicable.

Compared with conventional screening method such as mammography, MBI system 400 demonstrates higher sensitivity in lesion detection in the case of dense breast. In use, radiopharmaceuticals (such as technetium Tc 99m (99m Tc) sestamibi) may be injected into patient 102 a few minutes before image acquisition. The radiopharmaceuticals may get distributed in breast 104 as well as other parts of patient 102 (e.g., in a chest area close to breast 104, which may cause noises). During acquisition, breast 104 may be compressed to reduce its thickness for better penetration of gamma photons as well as to reduce its motion.

In an embodiment of MBI system 400, collimators 412 and 422 are placed on a same side of breast 104, but collimator 422 is positioned further away from breast 104 than collimator 412 (in the vertical direction Z of FIG. 4B). In addition, collimator 412 and detector 414 are placed closer to chest 106 than collimator 422 (in the horizontal direction X of FIG. 4B). In an embodiment, collimators 412 and 422 each include openings for passing through radiation emitted from breast 104. To reduce noises from other body parts not intended to be imaged (such as noises from areas of chest 106 that are close to breast 104), collimator 412 may have narrower and/or deeper openings than collimator 422. For instance, openings in collimator 412 may have a higher aspect ratio (of height to width, as described above with respect to imaging system 100) than openings in collimator 422 such that only photons with a narrow incident angle range may pass through collimator 412 to reach detector 414. Since collimator 412 is positioned close to chest 106, its openings may effectively block out noise emissions from areas of chest 106 that are close to breast 104. In some embodiments, the openings in collimator 422 and the positioning of collimators 412 and 422 on one side (e.g., lower side) of breast 104 are designed to ensure that radiation originated from above or to the left of collimator 412 positioned on the opposite side (e.g., upper side) of breast 104 will be blocked by shielding 416 and collimator 412 (on the upper side), as illustrated by the line E1 in FIG. 4B. In the case of only one imaging system 400 being employed, there may be a radiation shielding device positioned in such a way to ensure that. In an embodiment, openings in collimator 412 include parallel holes, and openings in collimator 422 include pinholes.

Figures 4C, 4D:
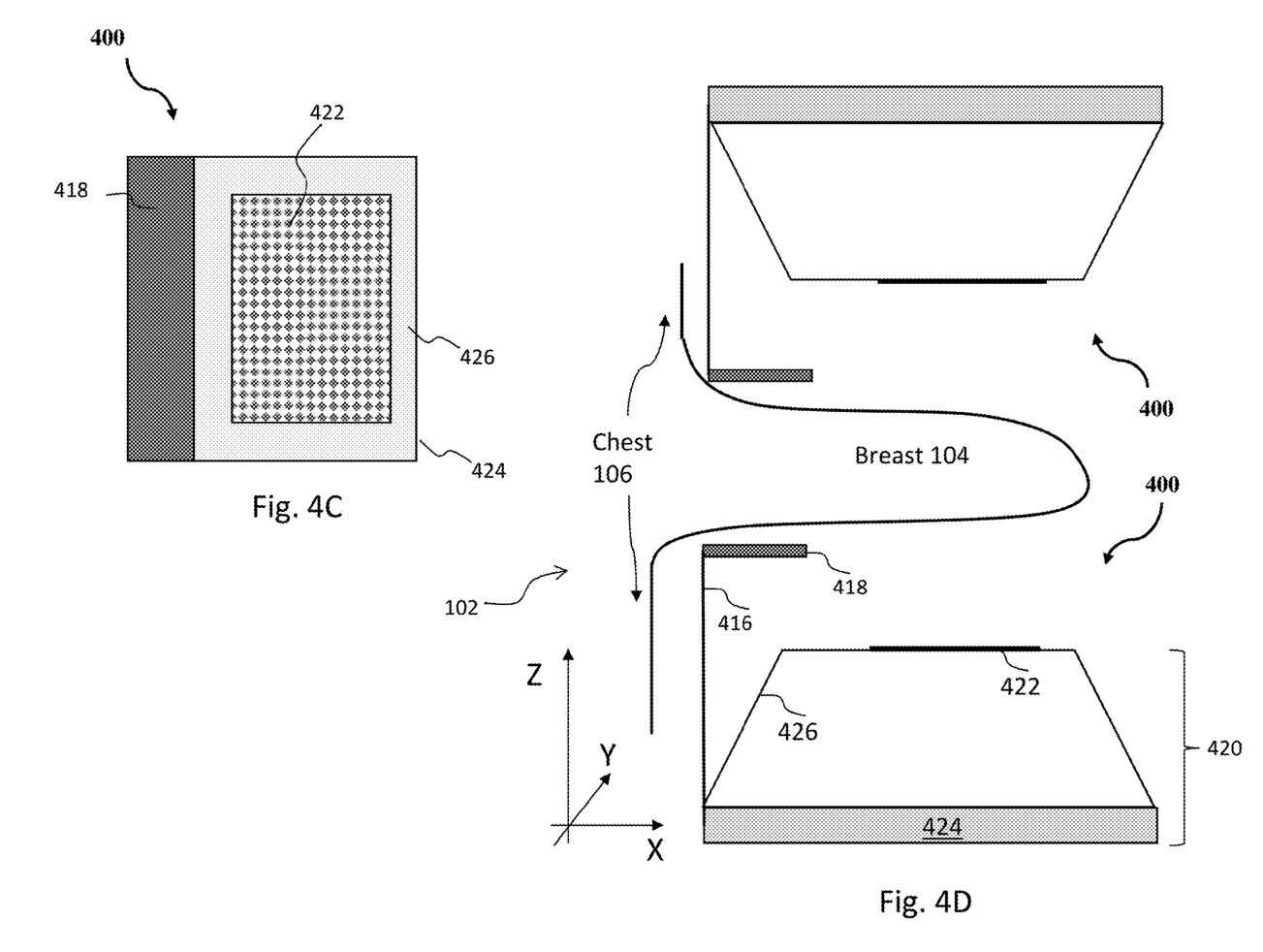
FIG. 4C is a schematic top view of another MBI system.
FIG. 4D is a cross-sectional view of two MBI systems shown in FIG. 4C, according to various aspects of the present disclosure.

Although MBI system 400 as shown in FIGS. 4A and 4B includes multiple collimators for imaging breast 104, it is understood that, in some embodiments, MBI system 400 may use a single collimator such as collimator 422, which works with other parts or has distinctive features to implement improved imaging of breast 104. Such distinctive features may also be used in the multiple collimator context to further improve imaging of breast 104. FIGS. 4C and 4D illustrate an example MBI system 450 with one or more FOV restrictors 418. For example, FOV restrictors 418 made of heavy metal may be placed between breast 104 and collimator 422. In an embodiment, FOV restrictor 418 is located on the side of collimator 422 that is proximal to chest 106 (that is, FOV restrictor 418 is closer to chest 106 than collimator 422). FOV restrictor 418 may be positioned similar to imager 410 in FIGS. 4A and 4B, and may replace imager 410 when image data from imager 410 is not needed in some applications. FOV restrictor 418 (sometimes called a view finder, as described above) may be positioned partially inside the FOV of collimator 422 so that the FOV restrictor blocks some photons from reaching collimator 422 that would otherwise reach collimator 422. The position of an FOV restrictor 418 may change during imaging, for example, in combination with imager motion, which is described further below.

In some embodiments, one or more radiation shielding devices, including 416 and 418 which replaces the FOV restrictor 418, may be placed on both sides of breast 104 against chest 106, as shown in FIGS. 4C and 4D. Radiation shielding devices 416 and 418 may help block radiation from hitting collimator 422, which may have multiple pinholes capable of receiving photons with a wide incident angle range. The optional radiation shielding device 418 may replace collimator 412 and detector 414 (in case image data from detector 414 is not needed) or may be deployed in addition to collimator 412 and detector 414. Even in a single-collimator MBI system 400, radiation shielding devices 416 and/or 418 may be placed on both sides of breast 104. For example, radiation shielding device 416 and/or 418 placed on the upper side of breast 104 may still help block photons traveling from above breast 104 or from chest 106 and prevent the photons from hitting collimator 422 placed at the lower side of breast 104. Although radiation shielding devices 416 and/or 418 are described with respect to MBI system 400, it should be understood that one or more similar radiation shielding devices may also be used in imaging system 100 (e.g., in addition to or in place of imager 110) in order to restrict the FOV of collimator 122.

In some embodiments, MBI system 400 is a breast gamma imaging system that employs one or more collimators having multi-pinholes. Compared with parallel holes, pinholes provide various benefits for breast imaging such as improving imaging resolution and sensitivity. Conventional MBI systems do not use multi-pinhole collimators because of the complexity of the image reconstruction algorithm and wide incident angles that allow photons from chest area to pass through and therefore degrade image quality. For example, pinholes can receive photons with a wider incident angle range. In an embodiment, collimator 422 using multi-pinholes is capable of receiving photons with an incident angle ($\beta$) equal to or greater than 30, 45, 60 degrees. In addition, the multiple pinholes may not be positioned on an equal spacing grid (that is, the pinholes may or may not be equally spaced on the plate of collimator 422). In addition, the height of pinholes (usually equal to the thickness of collimator plate) may be smaller than the height of parallel holes in a parallel-hole-based collimator. In an embodiment, collimator 422 using multi-pinholes is about 1 mm to about 3 mm thick. Furthermore, the number of pinholes may be quite large (e.g., more than 100). In an embodiment, the multi-pinhole collimator may be a coded aperture collimator. The multi-pinhole collimator may include apertures of different shapes or sizes.

In some embodiments, MBI system 400 includes one or more imagers that may move during imaging while patient 102 and breast 104 remain still. The motion of an imager (e.g., imager 410 or 420) may include shifting laterally (in x or y directions), or shifting vertically (in z direction), or tilting, or rotating, or combinations thereof. In some embodiments, when an imager moves, images are captured in a "step and shoot" fashion including, for example, the following operations: moving the imager to a first position, acquiring a first image from the first position for a period of time, moving the imager to a second position, and acquiring a second image from the second position for a certain period of time. The imager may move about breast 104 to other positions to repeat the operations. In some embodiments, during the motion, a distance between collimator 422 and detector 424 remains constant (unlike certain systems where the distance changes). In some embodiments, the distance between collimator 422 and detector 424 is large enough so that there is always multiplexing, i.e., photons may pass through different openings to reach the same surface area of detector 424; that is, images projected through the apertures are substantially overlapped. In an embodiment, at least half of images projected through an aperture overlap with images through at least one other aperture. In some embodiments, a 3D image of the breast comprising of multiple image slices (which represent object slices at different depths) is reconstructed based on one or more acquired images, and the 3D image is presented for viewing. This is beneficial because the contrast of lesion is higher in its respective slice of a 3D image than in a 2D image of the breast. In an embodiment, the number of slices is equal to or greater than the number of images acquired.

Although MBI system 400 is described with respect to molecular breast imaging, it is understood that principles disclosed herein apply to other breast imaging techniques using radiopharmaceuticals such as breast specific gamma imaging (BSGI) or scintimammography (SMM).

Figure 5:
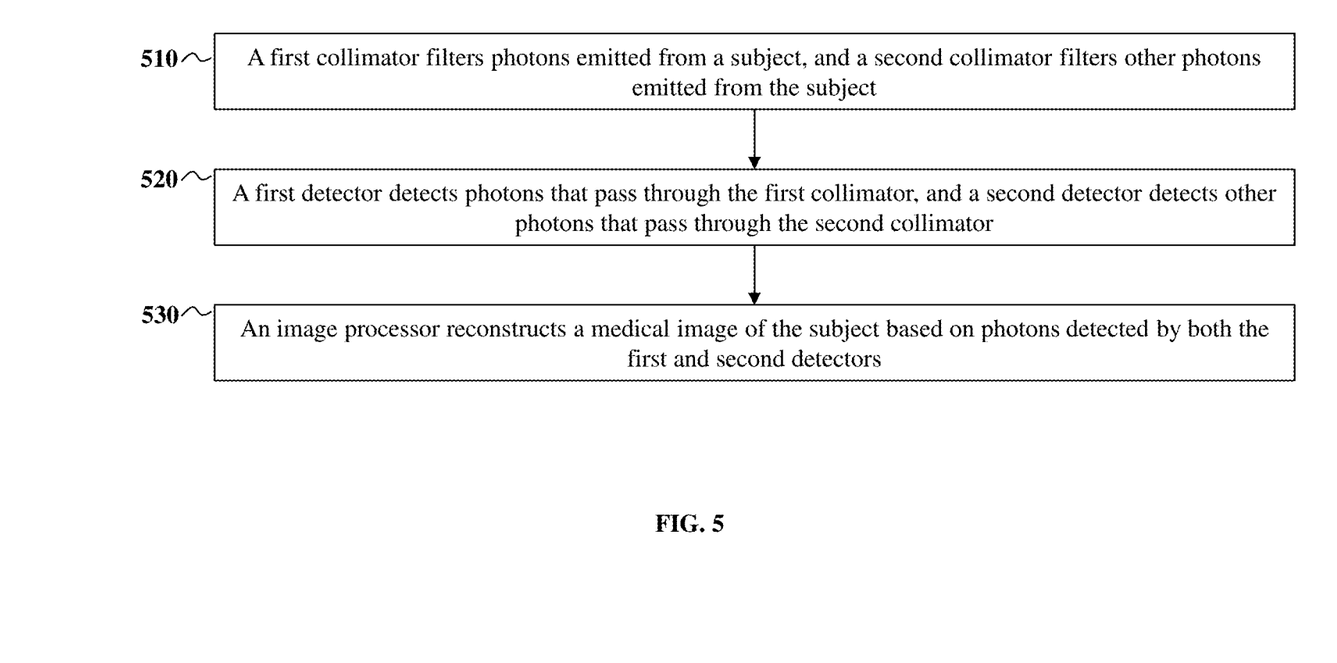
FIG. 5 is a flow chart of a method of examining a subject according to various aspects of the present disclosure.

Referring now to FIG. 5, a flow chart of a method 500 for examining a subject using molecular imaging is illustrated according to various aspects of the present disclosure. The method 500 is merely an example and is not intended to limit the present disclosure to what is explicitly illustrated in the method 500. Additional operations can be provided before, during, and after the method 500, and some operations described can be replaced, eliminated, or moved around for additional embodiments of the method. The method 500 is described below in conjunction with FIGS. 1-4.

At operation 510, a first collimator (e.g., collimator 112 or collimator 412) filters photons emitted from a subject such as patient 102, and a second collimator (e.g., collimator 122 or collimator 422) filters other photons emitted from the subject. In an embodiment, the first and second collimators are positioned such that their fields of view partially overlap in an overlapping volume. At operation 520, a first detector (e.g., detector 114 or detector 414) detects photons that pass through the first collimator, and a second detector (e.g., detector 124 or detector 424) detects other photons that pass through the second collimator.

At operation 530, an image processor (e.g., image processor 334) reconstructs a medical image of the subject based on photons detected by both the first and second detectors. In an embodiment, a first partial image is reconstructed based on photons that pass through the overlapping area and are detected by the first detector, and a second partial image is reconstructed based on photons detected by the second detector. The reconstruction of the second partial image optionally uses the first partial image as an initial estimate for the overlapping volume. Further, the reconstruction of the second partial image may update the first partial image using an iterative method. In another embodiment, an image of combined FOVs of first and second collimators may be reconstructed using photons detected by the first and second detectors simultaneously, and methods such as an MLEM method given in equation (1) herein may be used for reconstruction.

Although not intended to be limiting, one or more embodiments of the present disclosure provide many benefits for molecular imaging of a subject such as a patient. For example, the hybrid structure of multiple imagers allows a first imager (e.g., imager 110 or 410) to pick up peripheral photons (which increases imaging sensitivity), while reducing noises to be received by a second imager (e.g., imager 120 or 420). Therefore, system performance is improved.

The foregoing outlines features of several embodiments so that those of ordinary skill in the art may better understand the aspects of the present disclosure. Those of ordinary skill in the art should appreciate that they may readily use the present disclosure as a basis for designing or modifying other processes and structures for carrying out the same purposes and/or achieving the same advantages of the embodiments introduced herein. Those of ordinary skill in the art should also realize that such equivalent constructions do not depart from the spirit and scope of the present disclosure, and that they may make various changes, substitutions, and alterations herein without departing from the spirit and scope of the present disclosure. Accordingly, it is appropriate that the appended claims be construed broadly and in a manner consistent with the present disclosure.

What is claimed is:

1. A method for examining a subject using molecular imaging, the method comprising:
   filtering, by a first collimator, photons emitted from the subject;
   detecting, by a first detector, photons that pass through the first collimator;
   filtering, by a second collimator, photons emitted from the subject;
   detecting, by a second detector, photons that pass through the second collimator; and
   reconstructing, by an image processor, a medical image of the subject based on photons detected by both the first and second detectors, wherein the first and second collimators are positioned on a same side of the subject.

2. The method of claim 1, wherein the first and second collimators are positioned such that their fields of view partially overlap in an overlapping region.

3. The method of claim 2, wherein the reconstructing of the medical image comprises:
   reconstructing a first partial image based on photons that pass through the overlapping region and are detected by the first detector; and
   reconstructing a second partial image based on photons detected by the second detector, wherein the reconstructing of the second partial image uses the first partial image as an initial estimate for a volume of the overlapping region.

4. The method of claim 3, wherein the reconstructing of the second partial image further updates the first partial image using an iterative method.

5. The method of claim 1, wherein the medical image is an image of combined Field of Views (FOV) of the first and second collimators.

6. The method of claim 5, wherein the photons detected by the first and second detectors are detected simultaneously.

7. The method of claim 5, wherein the reconstructing comprises using a maximum likelihood expectation and maximization (MLEM) method during the reconstructing.

8. The method of claim 1, further comprising displaying the reconstructed medical image on a display device.

9. A method for examining a subject using molecular imaging, the method comprising:
   filtering, by a first collimator, radiation emitted from the subject;
   detecting, by a first detector, radiation that pass through the first collimator;
   filtering, by a second collimator, radiation emitted from the subject, wherein the first collimator partially blocks a field of view (FOV) of the second collimator;
   detecting, by a second detector, radiation that pass through the second collimator; and
   reconstructing, by an image processor, a medical image of the subject based on the radiation detected by both the first and second detectors, wherein the first and the second collimators are configured to be placed on a same side of the subject, and wherein the second collimator is positioned further away from the subject than the first collimator.

10. The method of claim 9, wherein the first and second collimators comprise first and second openings, respectively, for passing through radiation emitted from the subject, wherein the first and second openings have first and second aspect ratios, respectively, of height to width, and wherein the first aspect ratio is higher than the second aspect ratio.

11. The method of claim 9, further comprising:
    filtering, by a third collimator, radiation emitted from the subject;
    detecting, by a third detector, radiation that passes through the third collimator;
    filtering, by a fourth collimator, radiation emitted from the subject; and
    detecting, by a fourth detector, radiation that passes through the fourth collimator, wherein the third and fourth collimators are positioned on a same side of the subject that is opposite to the side of the subject where the first and second collimators are placed on.

12. The method of claim 10, wherein the openings of the first collimator include parallel holes and the openings of the second collimator include multiple pinholes.

13. The method of claim 9, wherein the medical image is an image of combined Field of Views (FOV) of the first and second collimators, and wherein the radiation detected by the first and second detectors are detected simultaneously.

14. The method of claim 9, further comprising displaying the reconstructed medical image on a display device, and wherein the reconstructing comprises using a maximum likelihood expectation and maximization (MLEM) method during the reconstructing.

15. The method of claim 9, wherein the second collimator and the second detector are configured to move about the subject while maintaining a constant distance between the second collimator and the second detector.

16. A method for examining a subject using molecular imaging, the method comprising:
    filtering, by a first collimator, radiation emitted from the subject;
    detecting, by a first detector, radiation that passes through the first collimator;
    filtering, by a second collimator, radiation emitted from the subject wherein the first collimator partially blocks a field of view (FOV) of the second collimator;
    detecting, by a second detector, radiation that pass through the second collimator; and
    reconstructing, by an image processor, a medical image of the subject based on the radiation detected by both the first and second detectors, wherein the first and the second collimators are configured to be placed on a same side of the subject, the second collimator is positioned further away from the subject than the first collimator, the first collimator comprises first openings for passing through radiation, the second collimator comprises second openings for passing through radiation, the first openings have a first aspect ratio of height to width, the second openings have a second aspect ratio of height to width, and wherein the first aspect ratio is higher than the second aspect ratio.

17. The method of claim 16, wherein the reconstructing comprises using a maximum likelihood expectation and maximization (MLEM) method during the reconstructing.

18. The method of claim 16, wherein the first openings include parallel holes, and the second openings include multiple pinholes in a plate.

19. The method of claim 16, wherein the first and second collimators are positioned such that their fields of view partially overlap in an overlapping region, wherein the reconstructing of the medical image comprises:
- reconstructing a first partial image based on the radiation that passes through the overlapping region and is detected by the first detector; and
- reconstructing a second partial image based on the radiation detected by the second detector, wherein the reconstructing of the second partial image uses the first partial image as an initial estimate for a volume of the overlapping region, and
- wherein the reconstructing of the second partial image further updates the first partial image using an iterative method.

20. The method of claim 19, wherein the medical image is an image of combined Field of Views (FOV) of the first and second collimators.

\* \* \* \* \*